(12) United States Patent
Hong et al.

(10) Patent No.: US 10,843,170 B2
(45) Date of Patent: Nov. 24, 2020

(54) SUPERABSORBENT POLYMER AND PREPARATION METHOD THEREOF

(71) Applicant: LG Chem, Ltd., Seoul (KR)

(72) Inventors: Yeon Woo Hong, Daejeon (KR); Seong Beom Heo, Daejeon (KR); Hyung Ki Yoon, Daejeon (KR); Dae Woo Nam, Daejeon (KR); Tae Hwan Jang, Daejeon (KR); Jun Kyu Kim, Daejeon (KR); Bo Hyun Seong, Daejeon (KR); Su Jin Kim, Daejeon (KR); Seon Jung Jung, Daejeon (KR); Ji Yoon Jeong, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 16/307,016

(22) PCT Filed: Feb. 2, 2018

(86) PCT No.: PCT/KR2018/001462
§ 371 (c)(1),
(2) Date: Dec. 4, 2018

(87) PCT Pub. No.: WO2018/147600
PCT Pub. Date: Aug. 16, 2018

(65) Prior Publication Data
US 2019/0217272 A1   Jul. 18, 2019

(30) Foreign Application Priority Data

Feb. 10, 2017 (KR) .................. 10-2017-0018678
Feb. 1, 2018 (KR) .................. 10-2018-0012910

(51) Int. Cl.
| | | |
|---|---|---|
| B01J 20/26 | (2006.01) | |
| C08J 3/24 | (2006.01) | |
| C08F 220/06 | (2006.01) | |
| C08F 4/04 | (2006.01) | |
| C08J 3/12 | (2006.01) | |
| C08F 2/50 | (2006.01) | |
| C08J 3/075 | (2006.01) | |
| A61L 15/24 | (2006.01) | |
| A61L 15/26 | (2006.01) | |
| A61L 15/42 | (2006.01) | |
| A61L 15/60 | (2006.01) | |
| B01J 20/22 | (2006.01) | |
| B01J 20/28 | (2006.01) | |
| B01J 20/30 | (2006.01) | |

(52) U.S. Cl.
CPC ............ *B01J 20/267* (2013.01); *A61L 15/24* (2013.01); *A61L 15/26* (2013.01); *A61L 15/425* (2013.01); *A61L 15/60* (2013.01); *B01J 20/22* (2013.01); *B01J 20/262* (2013.01); *B01J 20/28016* (2013.01); *B01J 20/3021* (2013.01); *B01J 20/3064* (2013.01); *B01J 20/3085* (2013.01); *C08F 2/50* (2013.01); *C08F 4/04* (2013.01); *C08F 220/06* (2013.01); *C08J 3/075* (2013.01); *C08J 3/12* (2013.01); *C08J 3/24* (2013.01); *C08J 3/245* (2013.01); *C08J 2333/02* (2013.01)

(58) Field of Classification Search
CPC .. B01J 20/267; B01J 20/3085; B01J 20/3078; B01J 20/3064; B01J 20/3021; B01J 20/28016; C08J 3/12; C08J 3/24; C08J 3/075; C08J 2333/08; C08J 2300/14; C08K 5/06; C08K 5/09
See application file for complete search history.

(56) References Cited

U.S. PATENT DOCUMENTS

| | | | |
|---|---|---|---|
| 5,563,218 A | 10/1996 | Rebre et al. | |
| 5,985,944 A | 11/1999 | Ishizaki et al. | |
| 6,750,262 B1 | 6/2004 | Hahnle et al. | |
| 2001/0038831 A1 | 11/2001 | Park et al. | |
| 2009/0239966 A1 | 9/2009 | Matsumoto et al. | |
| 2014/0193641 A1 | 7/2014 | Torii et al. | |
| 2015/0283284 A1 | 10/2015 | Azad et al. | |
| 2016/0354757 A1* | 12/2016 | Lee | A61L 15/60 |
| 2017/0081443 A1 | 3/2017 | Tanimura et al. | |
| 2017/0166707 A1 | 6/2017 | Jang et al. | |

FOREIGN PATENT DOCUMENTS

| | | |
|---|---|---|
| EP | 0615736 A1 | 9/1994 |
| EP | 0644211 A1 | 3/1995 |
| EP | 1637105 A1 | 3/2006 |
| EP | 1730218 B1 | 12/2010 |
| EP | 3260485 A1 | 12/2017 |
| EP | 3404057 A1 | 11/2018 |
| EP | 2797566 B1 | 6/2019 |
| JP | H11060729 A | 3/1999 |

(Continued)

OTHER PUBLICATIONS

Third Party Observation for PCT/KR2018/001462 submitted Jun. 4, 2019.
Bucholz et al., "Modern Superabsorbent Polymer Technology", Wiley-VCH, Copyright 1998, pp. 199-201.
Third Party Obersavtion for Application No. EP187518022 dated Jan. 3, 2020.
Search report from International Application No. PCT/KR2018/001462, dated May 21, 2018.
Schwalm, Reinhold, "UV Coatings: Basics, Recent Developments and New Applications." Dec. 21, 2006, p. 115.

(Continued)

*Primary Examiner* — Andrew J. Oyer
(74) *Attorney, Agent, or Firm* — Lerner, David, Littenberg, Krumholz & Mentlik, LLP

(57) ABSTRACT

A superabsorbent polymer having high centrifuge retention capacity and absorption rate prepared by using a particular foam stabilizer and a polymerization initiator. The foam stabilizer includes a sucrose ester and a polyalkylene oxide, and polymerization initiator includes a photoinitiator and a cationic azo-based initiator.

8 Claims, No Drawings

(56) References Cited

FOREIGN PATENT DOCUMENTS

| JP | 2001002821 A | 1/2001 |
|---|---|---|
| JP | 2002501563 A | 1/2002 |
| JP | 2002538254 A | 11/2002 |
| JP | 2003192732 A | 7/2003 |
| JP | 2005290121 A | 10/2005 |
| JP | 2006342306 A | 12/2006 |
| JP | 2011068821 A | 4/2011 |
| KR | 20010087042 A | 9/2001 |
| KR | 20070094741 A | 9/2007 |
| KR | 20140038998 A | 3/2014 |
| KR | 20160063956 A | 6/2016 |
| KR | 20160138998 A | 12/2016 |
| KR | 20160144902 A | 12/2016 |
| WO | 9617884 A1 | 6/1996 |
| WO | 2005063313 A1 | 7/2005 |
| WO | 2010046267 A1 | 4/2010 |

OTHER PUBLICATIONS

Odian, George, "Principles of Polymerization." A Wiley-Interscience Publication, Second Edition, 1981, p. 203.
Ahmed, Enas, M., "Hydrogel: Preparation, characterization, and applications: A review." Journal of Advanced Research, vol. 6 (Received Mar. 14, 2013; Revised Jul. 7, 2013; Accepted Jul. 8, 2013; Available online Jul. 18, 2013), pp. 105-121.
Extended European Search Report including Written Opinion for Application No. EP18751802.2 dated Mar. 25, 2019.

* cited by examiner

SUPERABSORBENT POLYMER AND PREPARATION METHOD THEREOF

CROSS-REFERENCE TO RELATED APPLICATIONS

The present application is a national phase entry under 35 U.S.C. § 371 of International Application No. PCT/KR2018/001462 filed on Feb. 2, 2018, which claims the benefit of Korean Patent Applications Nos. 10-2017-0018678 filed on Feb. 10, 2017 and 10-2018-0012910 filed on Feb. 1, 2018 the entire contents of which are incorporated herein by reference.

TECHNICAL FIELD

The present invention relates to a superabsorbent polymer having a high absorption rate, and a preparation method thereof.

BACKGROUND ART

A superabsorbent polymer (SAP) is a type of synthetic polymeric material that is capable of absorbing moisture from 500 to 1000 times its own weight. Various manufacturers have given it different names, such as SAM (Super Absorbent Material), AGM (Absorbent Gel Material), etc. Such superabsorbent polymers were initially practically applied in sanitary products, and now they are widely used not only for hygiene products such as disposable diapers for children, etc., but also for water retaining soil products for gardening, water stop materials for civil engineering and construction, sheets for raising seedlings, fresh-keeping agents for food distribution fields, materials for poultices, and the like.

In many cases, these superabsorbent polymers are widely used in sanitary materials such as diapers, sanitary pads, etc. Inside the sanitary materials, the superabsorbent polymer is generally distributed throughout pulp. However, recent efforts have been continuously made to provide thinner sanitary materials such as diapers having a thinner thickness, etc., and as part of that, diapers having a reduced content of pulp, and furthermore, diapers having no pulp, so-called pulpless diapers, are actively under development.

Such a sanitary material having a reduced content of pulp or having no pulp includes the superabsorbent polymer at a relatively high ratio, and the superabsorbent polymer particles are inevitably included as multiple layers in the sanitary materials. In order to allow all superabsorbent polymer particles included in multiple layers to more efficiently absorb a liquid such as urine, it is necessary for the superabsorbent polymer to basically exhibit high absorption performance and absorption rate.

Meanwhile, the absorption rate, one of important physical properties of the superabsorbent polymer, is associated with surface dryness of products in contact with the skin, such as diapers. Generally, the absorption rate may be improved by increasing surface area of the superabsorbent polymer.

For example, a method of forming a porous structure on the particle surface of the superabsorbent polymer by using a foaming agent is applied. However, since it is difficult to form a sufficient amount of the porous structure by using a general foaming agent, there is a drawback that the absorption rate is not greatly increased.

Another example is a method of increasing the surface area by regranulating fine particles obtained during a preparation process of the superabsorbent polymer to form non-uniform porous particles. This method may be employed to improve the absorption rate of the superabsorbent polymer, but there is a limitation in that centrifuge retention capacity (CRC) and absorbency under pressure (AUP) of the polymer become relatively low. That is, there is a trade-off between physical properties of the superabsorbent polymer such as absorption rate, centrifuge retention capacity, absorbency under pressure, etc. Accordingly, there is an urgent demand for a preparation method capable of improving these physical properties at the same time.

DETAILED DESCRIPTION OF THE INVENTION

Technical Problem

The present invention provides a superabsorbent polymer having a high absorption rate.

Further, the present invention provides a method of preparing the superabsorbent polymer.

Technical Solution

The present invention provides a method of preparing a superabsorbent polymer, the method including the steps of:

performing crosslinking polymerization of acrylic acid-based monomers having acidic groups which are at least partially neutralized in the presence of a polymerization initiator, a foam stabilizer, and an internal crosslinking agent to form a water-containing gel polymer;

drying, pulverizing, and size-sorting the water-containing gel polymer to form a base polymer powder; and performing surface-crosslinking of the base polymer powder by heat treatment in the presence of a surface crosslinking agent to form superabsorbent polymer particles, wherein the polymerization initiator includes a photoinitiator and a cationic azo-based initiator, and the foam stabilizer includes a sucrose ester and a polyalkylene oxide.

Further, the present invention provides a superabsorbent polymer including a base polymer which is obtained by polymerizing and internal crosslinking a monomer composition including acrylic acid-based monomers having acidic groups which are at least partially neutralized, and a surface-crosslinked layer which is formed on the surface of the base polymer, wherein centrifuge retention capacity (CRC) as measured in accordance with the EDANA method WSP 241.3 is 30 g/g or more, and an absorption rate as measured by a vortex method is 34 seconds or less.

Effect of the Invention

A superabsorbent polymer according to the present invention may exhibit high centrifuge retention capacity and absorption rate, because an azo-based compound having a particular structure is used as a polymerization initiator and a combination of a polyalkylene oxide and a sucrose ester is used as a foam stabilizer during polymerization to stably control foam generation in the polymerization process.

DETAILED DESCRIPTION OF THE EMBODIMENTS

The terminologies used herein are only for the purpose of describing exemplary embodiments and are not intended to limit the present invention. The singular forms used herein may be intended to include the plural forms as well, unless the context clearly indicates otherwise. It will be understood that the term "include", "equip" or "have", when used herein, specifies the presence of stated features, steps, components, or combinations thereof, but does not preclude the presence or addition of one or more other features, steps, components, or combinations thereof.

The present invention may be variously modified and have various forms, and specific embodiments of the present invention are exemplified and explained in this description. However, it is not intended to limit the present invention to the specific embodiments, and it must be understood that the present invention includes every modifications, equivalents, or replacements included in the spirit and technical scope of the present invention.

Hereinafter, a superabsorbent polymer and a preparation method thereof according to specific embodiments of the present invention will be described in more detail.

In superabsorbent polymers, centrifuge retention capacity (CRC), absorbency under pressure (AUL), and absorption rate are evaluated as important physical properties. To this end, a method of forming a large number of pores inside the superabsorbent polymer to rapidly absorb water or a method of reducing the particle size of the superabsorbent polymer is known. However, there is a limitation in the reduction of the particle size of the superabsorbent polymer, and formation of internal pores decreases gel strength, and therefore it is difficult to make the products thin.

Accordingly, it was suggested that a low-temperature foaming agent be used together with a high-temperature foaming agent to control the size and distribution of internal pores during the preparation of the superabsorbent polymer, thereby increasing the absorption rate. However, in order to control the size and distribution of pores, it is necessary to control a polymerization temperature, and thus the process becomes complicated, and it is difficult to prepare a base polymer having a high level of centrifuge retention capacity (CRC) and a high absorption rate (vortex time). Accordingly, there is still a demand for a method of preparing a superabsorbent polymer having more improved absorbency and absorption rate.

The present inventors found that when particular foam stabilizers are used in combination and a cationic azo-based polymerization initiator is used during polymerization, more stable and uniform foam distribution occurs, and consequently, a superabsorbent polymer showing high centrifuge retention capacity and a high absorption rate may be prepared, thereby completing the present invention.

Hereinafter, a superabsorbent polymer of the present invention and a preparation method thereof will be described in detail.

For reference, the "polymer" in the specification of the present invention refers to a polymerized state of acrylic acid-based monomers, and may cover those in any range of moisture content or particle size. Of the polymers, a polymer having a water content (moisture content) of about 40% by weight or more before drying after polymerization may be referred to as a water-containing gel polymer.

Further, the "base polymer" or "base polymer powder" refers to a powder prepared by drying and pulverizing the polymer.

In a method of preparing a superabsorbent polymer according to an aspect of the present invention, a water-containing gel polymer is first formed by polymerizing a monomer composition including acrylic acid-based monomers having acidic groups which are at least partially neutralized, a polymerization initiator, a foam stabilizer, and an internal crosslinking agent.

The acrylic acid-based monomer may have acidic groups which are at least partially neutralized, and preferably, those partially neutralized with an alkali substance such as sodium hydroxide, potassium hydroxide, ammonium hydroxide, etc. may be used. In this regard, a degree of neutralization of the acrylic acid-based monomer may be 40 mol % to 95 mol %, 40 mol % to 80 mol %, or 45 mol % to 75 mol %. The range of the neutralization degree may vary depending on final physical properties. An excessively high degree of neutralization renders the neutralized monomers precipitated, and thus polymerization may not occur readily, whereas an excessively low degree of neutralization not only deteriorates absorbency of the polymer but also endows the polymer with hard-to-handle properties, such as of elastic rubber.

Preferably, the acrylic acid-based monomer is a compound represented by the following Chemical Formula 1:

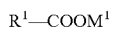   [Chemical Formula 1]

wherein $R^1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and a monovalent metal salt thereof, a divalent metal salt thereof, an ammonium salt thereof, and an organic amine salt thereof.

Further, a concentration of the acrylic acid-based monomer in the monomer composition may be properly controlled, in consideration of a polymerization time and reaction conditions, and the concentration may be preferably about 20% by weight to about 90% by weight, or about 40% by weight to about 70% by weight, which is for using the gel effect during the polymerization reaction in a high-concentration aqueous solution to eliminate a need for removing unreacted monomers after the polymerization and also for improving pulverization efficiency upon a subsequent pulverization process of the polymer. However, if the concentration of the monomer is too low, a yield of the superabsorbent polymer may become low. On the contrary, if the concentration of the monomer is too high, there is a process problem that a part of the monomers is precipitated, or pulverization efficiency is lowered upon pulverization of the polymerized water-containing gel polymer, and physical properties of the superabsorbent polymer may be deteriorated.

Meanwhile, the monomer composition may include an internal crosslinking agent for improving physical properties of the water-containing gel polymer. The crosslinking agent is one for internal crosslinking of the water-containing gel polymer, and is separately used in a subsequent process, independent of the surface crosslinking agent for surface crosslinking of the water-containing gel polymer.

Preferably, the internal crosslinking agent may be one or more selected from the group consisting of N,N'-methylenebisacrylamide, trimethylolpropane tri(meth)acrylate, ethylene glycol di(meth)acrylate, polyethylene glycol (meth)acrylate, polyethylene glycol di(meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triarylamine, ethylene glycol diglycidyl ether, propylene glycol, glycerin, and ethylene carbonate.

More preferably, when polyethylene glycol diacrylate (PEGDA) and/or hexanediol diacrylate (HDDA) are/is used as the internal crosslinking agent, more improved centrifuge retention capacity and absorption rate may be achieved.

The internal crosslinking agent may be added at a concentration of about 0.001 parts by weight to about 1 part by weight, based on 100 parts by weight of the acrylic acid-based monomer. If the concentration of the internal crosslinking agent is too low, the polymer may have a low absorption rate and low gel strength, undesirably. On the contrary, if the concentration of the internal crosslinking agent is too high, the polymer may have low absorption ability, which is not preferred for an absorbent.

Further, the present invention is characterized by including a cationic azo-based initiator as a polymerization initiator, and a sucrose ester and a polyalkylene oxide as a foam stabilizer, in addition to the monomer composition and the internal crosslinking agent.

The polyalkylene oxide, along with the sucrose ester, plays a role in more stably forming foams during the polymerization process, and therefore, the water-containing gel including the foams may have a high centrifuge retention capacity and a high absorption rate.

Specifically, the polyalkylene oxide may be, for example, one or more selected from the group consisting of polyethylene oxide (PEO), polypropylene oxide (PPO), a polyethylene oxide-polypropylene oxide (PEO-PPO) diblock copolymer, and a polyethylene oxide-polypropylene oxide-polyethylene oxide (PEO-PPO-PEO) triblock copolymer, and the PEO-PPO-PEO triblock copolymer may preferably be used, but is not limited thereto.

According to an embodiment of the present invention, a weight average molecular weight of the polyalkylene oxide may be about 500 g/mol or more and less than about 3000 g/mol, or about 1000 g/mol to about 2700 g/mol, and the PEO-PPO-PEO triblock copolymer, in which a ratio of ethylene oxide (EO) in the polyalkylene oxide is 20% by weight to 80% by weight or 20% by weight to 60% by weight, may be more preferably used.

When the polyalkylene oxide having a weight average molecular weight within the above range is used, physical properties associated with absorption rate, such as vortex time, etc., may be improved.

The polyalkylene oxide may be added at a concentration of about 0.001 parts by weight to about 1 part by weight, or about 0.01 parts by weight to about 0.5 parts by weight, based on 100 parts by weight of the acrylic acid-based monomer.

If the concentration of the polyalkylene oxide is too low, its function as the foam stabilizer is insignificant, and thus it is difficult to achieve the effect of improving the absorption rate. On the contrary, if the concentration of the polyalkylene oxide is too high, there is a problem that the centrifuge retention capacity and absorption rate may be reduced or surface tension may be reduced. Surface tension is associated with dryness when the superabsorbent polymer is applied to absorbent articles such as diapers. As the surface tension of the superabsorbent polymer is decreased, the amount of water that leaks back out after being absorbed by the superabsorbent polymer is increased.

The sucrose ester which is used together with the polyalkylene oxide as the foam stabilizer may be exemplified by sucrose stearate, sucrose isobutyrate, sucrose palmitate, sucrose laurate, etc., and among them, two or more thereof may be used in combination, but the present invention is not limited thereto. Preferably, sucrose stearate may be used.

The sucrose ester may be added at a concentration of about 0.001 parts by weight to about 0.1 s part by weight, or about 0.005 parts by weight to about 0.05 parts by weight, based on 100 parts by weight of the acrylic acid-based monomer.

If the concentration of the sucrose ester is too low, its function as the foam stabilizer is insignificant, and thus it is difficult to achieve the effect of improving the absorption rate. On the contrary, if the concentration of the sucrose ester is too high, the centrifuge retention capacity and absorption rate may be reduced during polymerization, which may be undesirable.

Further, the sucrose ester may be preferably used at a ratio of about 1 part by weight to about 50 parts by weight, or about 1 part by weight to about 10 parts by weight, based on 100 parts by weight of the polyalkylene oxide.

The foam stabilizer including the polyalkylene oxide and the sucrose ester may be added in an amount of about 0.001 parts by weight to about 2 parts by weight, or about 0.01 parts by weight to about 1 part by weight, based on 100 parts by weight of the acrylic acid-based monomer.

When the cationic azo-based initiator is used together with the sucrose ester and the polyalkylene oxide, the superabsorbent polymer to be prepared may be allowed to exhibit a fast vortex absorption rate in a high CRC region, and at the same time, a content of residual monomers may be reduced in the polymerization process.

Specifically, when the cationic azo-based initiator is used together with the sucrose ester and the polyalkylene oxide, the content of residual monomers in the base polymer may be about 450 ppm or less, or about 300 ppm to about 450 ppm, preferably about 350 ppm or more and about 400 ppm or less, as measured by the EDANA method WSP 210.3, and about 350 ppm or less, or about 250 ppm to about 350 ppm, and preferably about 250 ppm or more and about 300 ppm or less, based on the surface-treated superabsorbent polymer.

The cationic azo-based initiator to be applicable may be exemplified by an azo nitrile-based initiator (trade name: Wako V-501), an azo amide-based initiator (trade name: Wako VA-086), an azo amidine-based initiator (trade name: Wako VA-057, V-50), and an azo imidazoline-based initiator (trade name: Wako VA-061, VA-044), etc., but the present is not limited thereto.

The cationic azo-based initiator may be used together with a known polymerization initiator which is generally used in the preparation of the superabsorbent polymer, as follows.

As the polymerization initiator, a thermal polymerization initiator or a photo-polymerization initiator may be used depending on a polymerization method. However, even though the photo-polymerization is performed, a certain amount of heat is generated by UV irradiation or the like, and is also generated with an exothermic polymerization reaction. Therefore, the thermal polymerization initiator may be further included even though photo-polymerization is performed.

The photo-polymerization initiator may be, for example, one or more compounds selected from the group consisting of benzoin ether, dialkyl acetophenone, hydroxyl alkyl ketone, phenyl glyoxylate, benzyl dimethyl ketal, acyl phosphine, and α-aminoketone. As the specific example of acyl phosphine, commercial Lucirin TPO, namely, 2,4,6-trimethyl-benzoyl-trimethyl phosphine oxide, may be used. More various photo-polymerization initiators are well-disclosed in "UV Coatings: Basics, Recent Developments and New Application (Elsevier, 2007)" written by Reinhold Schwalm, p 115, which may serve as a reference.

Further, the thermal polymerization initiator may be one or more compounds selected from the group consisting of persulfate-based initiators, azo-based initiators, hydrogen peroxide, and ascorbic acid. Specific examples of the persulfate-based initiators may include sodium persulfate ($Na_2S_2O_8$), potassium persulfate ($K_2S_2O_8$), ammonium persulfate (($NH_4)_2S_2O_8$), etc.

Further, specific examples of the azo-based initiators may include 2,2-azobis(2-amidinopropane) dihydrochloride, 2,2-azobis-(N,N-dimethylene)isobutyramidine dihydrochloride, 2-(carbamoylazo)isobutyronitrile, 2,2-azobis(2-[2-imidazolin-2-yl]propane)dihydrochloride, 4,4-azobis-(4-cyanovaleric acid), etc. More various thermal polymerization initiators are well-disclosed in "Principle of Polymerization (Wiley, 1981)" written by Odian, p 203, which may serve as a reference.

The polymerization initiator may be added at a concentration of about 0.001 parts by weight to about 1 part by weight, based on 100 parts by weight of the acrylic acid-based monomer. That is, if the concentration of the polymerization initiator is too low, the polymerization rate may become low and thus a large amount of residual monomers may be undesirably extracted from the final product. On the contrary, if the concentration of the polymerization initiator is too high, the polymer chains constituting the network become short, and thus the content of water-soluble components is increased and physical properties of the polymer may deteriorate, such as a reduction in absorbency under load, which is undesirable.

According to an embodiment of the present invention, the monomer composition may further include one or more foaming agents selected from the group consisting of sodium bicarbonate, sodium carbonate, potassium bicarbonate, potassium carbonate, calcium bicarbonate, calcium bicarbonate, magnesium bicarbonate, and magnesium carbonate.

In addition, the monomer composition may further include an additive such as a thickener, a plasticizer, a storage stabilizer, an antioxidant, etc., as needed.

Further, the monomer composition may be in the form of a solution, which is prepared by dissolving the raw materials including the acrylic acid-based monomers, the polymerization initiator, the internal crosslinking agent, the sucrose ester, and the foam stabilizers in a solvent.

In this regard, any solvent may be used as an applicable solvent without limitations in the constitution, as long as it is able to dissolve the above raw materials. For example, water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethyl ether, toluene, xylene, butyrolactone, carbitol, methyl cellosolve acetate, N,N-dimethylacetamide, or a mixture thereof may be used as the solvent. The amount of the solvent may be controlled at a weight ratio of 1 to 5 times with respect to the content of the acrylic acid-based monomer, in consideration of the polymerization heat control.

On the other hand, formation of the water-containing gel polymer by polymerizing and crosslinking the monomer composition may be performed by a general polymerization method known in the art to which the present invention pertains, and the process is not particularly limited. A non-limiting example of the polymerization method is largely classified into thermal polymerization and photo-polymerization according to a polymerization energy source, and the thermal polymerization may be carried out in a reactor like a kneader equipped with agitating spindles, while the photo-polymerization may be carried out in a reactor equipped with a movable conveyor belt.

For example, the monomer composition is injected into a reactor like a kneader equipped with the agitating spindles, and thermal polymerization is performed by providing hot air thereto or heating the reactor so as to obtain the water-containing gel polymer. In this regard, the water-containing gel polymer may be obtained as particles having a size of centimeters or millimeters when it is discharged from the outlet of the reactor, according to the type of agitating spindles equipped in the reactor. The water-containing gel polymer may be obtained in various forms according to the concentration of the monomer composition fed thereto, the feeding speed, or the like, and the water-containing gel polymer having a weight average particle size of 2 mm to 50 mm may be generally obtained.

As another example, when the photo-polymerization of the monomer composition is carried out in a reactor equipped with a movable conveyor belt, the water-containing gel polymer may be obtained in the form of a sheet. In this regard, a thickness of the sheet may vary according to the concentration of the monomer composition fed thereto and the feeding speed, and the polymer sheet is preferably controlled to have a thickness of about 0.5 cm to about 5 cm in order to uniformly polymerize the entire sheet and secure production speed.

The water-containing gel polymer formed by the above method may have a water content of about 40% by weight to about 80% by weight. In terms of optimizing the efficiency of a drying step described below, it is preferable that the water content of the water-containing gel polymer is controlled within the above range.

The water content, as used herein, means a water content in the total weight of the water-containing gel polymer, which may be obtained by subtracting the weight of the dry polymer from the weight of the water-containing gel polymer. Specifically, the water content may be defined as a value calculated by measuring the weight loss according to evaporation of water in the polymer during the drying process of increasing the temperature of the polymer with infrared heating. In this regard, the drying conditions may be set as follows: the temperature is increased from room temperature to about 180° C. and then the temperature is maintained at 180° C., and a total drying time is determined as 40 min, including 5 min for the temperature rising step.

The water-containing gel polymer obtained by the above-described step is subjected to a drying process in order to provide the water-containing gel polymer with absorbency. In order to increase efficiency of the drying process, the water-containing gel polymer is subjected to a step of (coarsely) pulverizing the water-containing gel polymer, before the drying process.

A non-limiting example of a pulverizing device applicable to the coarse pulverization may include a vertical pulverizer, a turbo cutter, a turbo grinder, a rotary cutter mill, a cutter mill, a disc mill, a shred crusher, a crusher, a chopper, a disc cutter, etc.

In this regard, the coarse pulverization may be performed so that the water-containing gel polymer has a particle size of about 2 mm to about 10 mm That is, to increase the drying efficiency, the water-containing gel polymer is preferably pulverized to have a particle size of about 10 mm or less. However, excessive pulverization may cause agglomeration between particles, and therefore, the water-containing gel polymer is preferably pulverized to have a particle size of about 2 mm or more.

In the coarse pulverization, the polymer may stick to the surface of the pulverizing device because it has a high water content. In order to minimize this phenomenon, steam, water, a surfactant, an anti-agglomeration agent (e.g., clay, silica, etc.), a persulfate-based initiator, an azo-based initiator, hydrogen peroxide, a thermal polymerization initiator, an epoxy-based crosslinking agent, a diol-based crosslinking agent, a crosslinking agent including 2-functional or 3 or more-functional acrylate, or a mono-functional crosslinking agent including a hydroxyl group may be added during the coarse pulverization, if necessary.

The water-containing gel polymer coarsely pulverized by the above-described step is subjected to a drying process. As the water-containing gel polymer is supplied to the drying step in a state of being pulverized into particles of about 2 mm to about 10 mm through the above-described step, drying may be performed with higher efficiency.

The drying of the coarsely pulverized water-containing gel polymer may be performed at a temperature of about 120° C. to about 250° C., preferably about 140° C. to about 200° C., and more preferably about 150° C. to about 190° C. In this regard, the drying temperature is defined as a temperature of a heating medium provided for drying, or a temperature of a drying reactor including the heating medium and the polymer during the drying process. If the drying temperature is low, and therefore the drying time becomes long, the process efficiency may be decreased. In order to prevent this problem, the drying temperature is preferably 120° C. or higher. On the contrary, when the drying temperature is higher than necessary, the surface of the water-containing gel polymer is excessively dried, and thus there is a concern about generation of fine particles during the subsequent pulverization process and deterioration of the physical properties of the finally formed polymer. In order to prevent this problem, therefore, the drying temperature is preferably about 250° C. or lower.

In this regard, the drying time in the drying step is not particularly limited, but may be controlled to about 20 min to about 90 min at the above drying temperature, in consideration of process efficiency and physical properties of the polymer.

The drying may be carried out by using a general medium, and for example, the coarsely pulverized water-containing gel polymer may be supplied with hot air, or irradiated with infrared rays, microwaves, ultraviolet rays, or the like.

The drying is preferably performed so that the water content of the dried polymer may be about 0.1% by weight to about 10% by weight. In other words, if the water content of the dried polymer is less than about 0.1% by weight, production costs may be increased and degradation of the crosslinked polymer may undesirably occur due to excessive drying. If the water content of the dried polymer is more than about 10% by weight, defective products may be undesirably produced in a subsequent process.

A step of pulverizing the polymer which is dried by the above-described step is performed. The pulverization step is a step of optimizing the surface area of the dried polymer, whereby the pulverized polymer has a particle size of about 150 μm to about 850 μm.

In this regard, a pulverizing device may include a generally used pin mill, hammer mill, screw mill, roll mill, disc mill, jog mill, or the like. Further, a step of selectively size-sorting the polymer particles having a particle size of 150 μm to 850 μm from the polymer particles obtained through the pulverization step may be further performed in order to manage physical properties of the superabsorbent polymer finally produced.

The polymer (base polymer) that is polymerized, dried, and pulverized by the processes of the present invention may have centrifuge retention capacity (CRC) of about 35 g/g or more, about 37 g/g or more, or about 40 g/g or more and about 50 g/g or less, about 45 g/g or less, or about 42 g/g or less, as measured in accordance with the EDANA method WSP 241.3.

The polymer may have an absorption rate of 42 s or less, or about 40 s or less, and about 25 s or more, about 30 s or more, or about 35 s or more, as measured by a vortex method.

Thereafter, a step of modifying the surface of the polymer which is pulverized by the above-described step is performed, in which the base polymer powder is heat-treated in the presence of a crosslinking agent including a surface crosslinking agent to form surface-crosslinked superabsorbent polymer particles.

The surface modification is a step of producing the superabsorbent polymer having more improved physical properties by inducing surface-crosslinking of the surface of the pulverized polymer in the presence of the surface crosslinking agent. A surface crosslinking layer may be formed on the surface of the pulverized polymer particles by the surface-modification.

The surface modification (surface-crosslinking reaction) may be performed by a general method of increasing crosslinking density of the surface of the polymer particle, and for example, a solution including the surface crosslinking agent may be mixed with the pulverized polymer to allow crosslinking reaction.

Here, as long as the surface crosslinking agent is a compound that may react with the functional group of the polymer, it may be used without limitation in the constitution thereof. Non-limiting examples of the surface crosslinking agent may include one or more compounds selected from the group consisting of ethylene glycol diglycidyl ether, polyethylene glycol diglycidyl ether, glycerol polyglycidyl ether, propylene glycol diglycidyl ether, polypropylene glycol diglycidyl ether, ethylene glycol, diethylene glycol, propylene glycol, triethylene glycol, tetraethylene glycol, propane diol, dipropylene glycol, polypropylene glycol, glycerin, polyglycerin, butanediol, heptanediol, hexanediol, trimethylol propane, pentaerythritol, sorbitol, calcium hydroxide, magnesium hydroxide, aluminum hydroxide, iron hydroxide, calcium chloride, magnesium chloride, aluminum chloride, and iron chloride.

In this regard, the content of the surface crosslinking agent may be properly controlled according to the type of the crosslinking agent or reaction conditions, and the content is preferably about 0.001 parts by weight to about 5 parts by weight, based on 100 parts by weight of the pulverized polymer. If the content of the surface crosslinking agent is too low, surface modification may hardly occur to deteriorate physical properties of the final polymer. On the contrary, if the surface crosslinking agent is excessively used, excessive surface crosslinking reaction may occur, undesirably leading to deterioration in absorption ability of the polymer.

Meanwhile, the surface modification step may be performed by a general method, such as a method of feeding the surface crosslinking agent and the pulverized polymer to the reactor and mixing them, a method of spraying the surface crosslinking agent onto the pulverized polymer, or a method of mixing the pulverized polymer and the surface crosslinking agent while continuously feeding them to a mixer being continuously operated.

The surface crosslinking agent may be added with water. When the surface crosslinking agent is added together with water, the surface crosslinking agent may be evenly dispersed, agglomeration of the polymer particles may be prevented, and the penetrating depth of the surface crosslinking agent into the polymer particles may be optimized. Considering these purposes and effects, the amount of water added with the surface crosslinking agent may be about 0.5 parts by weight to about 10 parts by weight, based on 100 parts by weight of the pulverized polymer.

The surface crosslinking may be performed at a temperature of about 175° C. to about 200° C., and may be continuously performed after the drying and pulverizing steps which are performed at a relatively high temperature. More preferably, the surface crosslinking may be performed at a temperature of about 180° C. to about 195° C.

In this regard, the surface crosslinking reaction may be performed for about 1 min to about 120 min, or about 1 min to about 100 min, or about 10 min to about 60 min That is, in order to prevent a reduction in physical properties due to deterioration of the polymer particles by excessive reaction while inducing the minimal surface crosslinking reaction, the surface crosslinking reaction may be performed under the above-described conditions.

Another aspect of the present invention provides a superabsorbent polymer including a base polymer obtained from polymerization and internal crosslinking of a monomer composition including acrylic acid-based monomers having acidic groups which are at least partially neutralized, and a surface crosslinked layer formed on the surface of the base polymer, wherein the base polymer has centrifuge retention capacity (CRC) of 35 g/g or more, as measured in accordance with the EDANA method WSP 241.3, and an absorption rate of 40 s or less, as measured by a vortex method.

Accordingly, in the present invention, foams generated during the preparation process of the superabsorbent polymer may be stabilized by using a particular foam stabilizer and the sucrose ester at the same time during polymerization, thereby achieving high centrifuge retention capacity and absorption rate.

Preferably, the acrylic acid-based monomer is a compound represented by the following Chemical Formula 1:

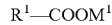 [Chemical Formula 1]

wherein $R^1$ is an alkyl group containing an unsaturated bond and having 2 to 5 carbon atoms, and $M^1$ is a hydrogen atom, a monovalent or divalent metal, an ammonium group, or an organic amine salt.

Preferably, the acrylic acid-based monomer may include one or more selected from the group consisting of acrylic acid, methacrylic acid, and a monovalent metal salt thereof, a divalent metal salt thereof, an ammonium salt thereof, and an organic amine salt thereof.

Here, the acrylic acid-based monomer may have acidic groups which are at least partially neutralized, and preferably, those partially neutralized with an alkali substance such as sodium hydroxide, potassium hydroxide, ammonium hydroxide, etc. may be used. In this regard, a degree of neutralization of the acrylic acid-based monomer may be about 40 mol % to about 95 mol %, about 40 mol % to about 80 mol %, or about 45 mol % to about 75 mol %. The range of the neutralization degree may vary depending on final physical properties. An excessively high degree of neutralization renders the neutralized monomers precipitated, and thus polymerization may not occur readily, whereas an excessively low degree of neutralization not only deteriorates absorbency of the polymer but also endows the polymer with hard-to-handle properties, such as of elastic rubber.

Preferably, the crosslinked polymer may be internally crosslinked by one or more internal crosslinking agents selected from the group consisting of N,N'-methylenebisacrylamide, trimethylolpropane tri(meth)acrylate, ethylene glycol di(meth)acrylate, polyethylene glycol (meth)acrylate, polyethylene glycol di(meth)acrylate, propylene glycol di(meth)acrylate, polypropylene glycol (meth)acrylate, butanediol di(meth)acrylate, butylene glycol di(meth)acrylate, diethylene glycol di(meth)acrylate, hexanediol di(meth)acrylate, triethylene glycol di(meth)acrylate, tripropylene glycol di(meth)acrylate, tetraethylene glycol di(meth)acrylate, dipentaerythritol pentaacrylate, glycerin tri(meth)acrylate, pentaerythritol tetraacrylate, triarylamine, ethylene glycol diglycidyl ether, propylene glycol, glycerin, and ethylene carbonate. More preferably, the crosslinked polymer may be internally crosslinked by polyethylene glycol diacrylate (PEGDA) and/or hexanediol diacrylate (HDDA).

In the present invention, the crosslinked polymer may have centrifuge retention capacity (CRC) of about 35 g/g or more, about 36 g/g or more, or about 40 g/g or more, as measured in accordance with the EDANA method WSP 241.3. An upper limit of the centrifuge retention capacity (CRC) is not particularly limited, but it may be, for example, about 50 g/g or less, about 45 g/g or less, or about 42 g/g or less.

Further, the crosslinked polymer may have an absorption rate of about 40 s or less, about 39 s or less, or about 37 s or less, as measured by a vortex method. A lower limit of the absorption rate is not particularly limited, but it may be, for example, about 15 s or more, about 20 s or more, or about 30 s or more.

In this regard, the centrifuge retention capacity and absorption rate are values measured for the base polymer (base resin) which is a powdery crosslinked polymer obtained by drying and pulverizing after polymerization of the monomer composition, before formation of the surface-crosslinked layer on the surface of the crosslinked polymer.

When the surface-crosslinked layer is formed on the base polymer, absorbency under pressure (AUP) and absorption rate (vortex time) are generally improved, but centrifuge retention capacity (CRC) is reduced. Therefore, considering the decreasing tendency of centrifuge retention capacity, it is very important to prepare the base polymer having high centrifuge retention capacity in order to secure the physical properties of the final product. The superabsorbent polymer having the surface-crosslinked layer which is formed on the base polymer having high centrifuge retention capacity has little concern about the reduction of centrifuge retention capacity and has improved absorbency under pressure and absorption rate at the same time, and therefore, it is possible to obtain a polymer having higher quality.

For example, the superabsorbent polymer having the surface-crosslinked layer formed on the crosslinked polymer (base polymer) having the above centrifuge retention capacity and absorption rate may have centrifuge retention capacity (CRC) of about 30 g/g or more, about 31 g/g or more, or about 34 g/g or more, and about 45 g/g or less, about 40 g/g or less, or about 36 g/g or less, as measured in accordance with the EDANA method WSP 241.3.

Further, the superabsorbent polymer having the surface-crosslinked layer formed on the base polymer may have an absorption rate of about 34 s or less, about 33 s or less, or about 30 s or less, and about 10 s or more, about 15 s or more, or about 20 s or more, as measured by a vortex method.

The centrifuge retention capacity (CRC) may be measured in accordance with the EDANA method WSP 241.3, and may be represented by the following Equation 1:

CRC (g/g)={[$W_2$(g)-$W_1$(g)]/$W_0$(g)}-1    [Equation 1]

wherein $W_0$ (g) is the weight (g) of the polymer, $W_1$ (g) is the weight (g) of the apparatus, which is measured after draining water off at 250 G for 3 minutes using a centrifuge without the polymer, and $W_2$ (g) is the weight (g) of the apparatus including the polymer, which is measured after immersing the polymer in a physiological saline solution of 0.9% by weight at room temperature for 30 minutes and draining water off at 250 G for 3 minutes using a centrifuge.

In the measurement of the absorption rate by the vortex method, 50 ml of the physiological saline solution and a magnetic bar were put in a 100 ml beaker, a stirring speed of the magnetic bar was set at 600 rpm by using a stirrer, and then 2.0 g of the polymer was added to the physiological saline solution under stirring, and at this time, a time (unit: s) taken for the vortex in the beaker to disappear was measured as the vortex time.

Further, when the superabsorbent polymer is swollen by a physiological saline, specifically, 0.9% by weight of a sodium chloride aqueous solution, its surface tension value measured for the corresponding sodium chloride aqueous solution may preferably be about 40 mN/m or more, about 40 mN/m to about 70 mN/m, or about 60 mN/m to about 70 mN/m.

The surface tension may be measured, for example, at room temperature of 23±2° C. by using a tension meter. A specific method of measuring the surface tension is described in an example below.

The surface tension of the superabsorbent polymer is a physical property which is distinct from centrifuge retention capacity, absorbency under pressure, liquid permeability, etc., and may be a measure capable of evaluating leakage of urine from a diaper including the superabsorbent polymer. The surface tension is measured for saline after the superabsorbent polymer is swollen in the corresponding saline, and if the surface tension of the superabsorbent polymer is low, there is a high possibility of leakage of urine from diapers which are prepared by including the superabsorbent polymer. According to the superabsorbent polymer of an embodiment, the superabsorbent polymer has an appropriate range of surface tension while maintaining high liquid permeability, etc., thereby reducing the possibility of leakage. Thus, it is possible to produce high-quality sanitary materials.

If the surface tension of the superabsorbent polymer is too low, leakage of urine, that is, rewetting, may increase, and if the surface tension of the superabsorbent polymer is too high, the surface-crosslinked layer is not uniformly formed, and thus physical properties such as liquid permeability, etc. may be deteriorated.

Hereinafter, the actions and effects of the present invention will be described in more detail with reference to specific examples. However, these examples are for illustrative purposes only, and the scope of the present invention is not intended to be limited by these examples.

EXAMPLES

Examples

Example 1

1-1. Preparation of Base Polymer 100 parts by weight of acrylic acid, 83.3 parts by weight of 50% caustic soda (NaOH), 89.8 parts by weight of water, and the following components were mixed to prepare a monomer composition.

Internal crosslinking agent: 0.27 parts by weight (2700 ppmw) of polyethylene glycol diacrylate (PEGDA; Mw=400) and 0.054 parts by weight (540 ppmw) of polyethylene glycol diacrylate (PEGDA; Mw=200)

Polymerization initiator: 0.1 parts by weight (1000 ppmw) of cationic azo-based initiator (V50), 0.02 parts by weight (300 ppmw) of hydrogen peroxide ($H_2O_2$), 0.05 parts by weight (500 ppmw) of ascorbic acid, 0.2 parts by weight (2000 ppmw) of potassium persulfate (KPS)

Foam stabilizer: 0.016 parts by weight (160 ppmw) of sucrose stearate (S1670), and 0.16 parts by weight (1600 ppmw) of a polyalkylene oxide (PEO-PPO-PEO triblock copolymer, Mw: 2550)

The monomer composition was subjected to thermal polymerization reaction to obtain a polymerized sheet. The polymerized sheet was taken out and cut to a size of 3 cm×3 cm, and subjected to a chopping process by using a meat chopper to prepare crumbs. The crumbs were dried in an oven capable of shifting airflow up and down. The crumbs were uniformly dried by flowing hot air at 180° C. from the bottom to the top for 15 minutes and from the top to the bottom for 15 minutes. After drying, the dried product was allowed to have a water content of 2% or less. After drying, the product was pulverized by using a pulverizer and sorted by size, and particles having a size of about 150 μm to about 850 μm were selected to prepare a base polymer.

1-2. Preparation of Superabsorbent Polymer

To 100 parts by weight of the base polymer prepared in 1-1, 4 parts by weight of water, 4 parts by weight of methanol, 0.3 parts by weight of ethylene glycol diglycidyl ether, 0.06 parts by weight of silica (Aerosil 200), and 0.2 parts by weight of oxalic acid were added and mixed, and allowed to react at a surface crosslinking temperature of 140° C. for 40 minutes, and pulverized. Then, a sieve was used to select a surface-treated superabsorbent polymer having a particle size of 150 μm to 850 μm.

Examples 2 to 7 and Comparative Examples 1 to 6

Superabsorbent polymers were prepared in the same manner as in Example 1, except for varying the contents of individual components.

Examples 8 and 9 and Comparative Example 8

Superabsorbent polymers were prepared in the same manner as in Example 1, except for using a polyalkylene oxide (PEO-PPO-PEO triblock copolymer) having a different weight average molecular weight from that of the foam stabilizer and varying the content thereof.

The contents of individual components used in examples and comparative examples are as in the following Table 1.

TABLE 1

| | PEO-PPO-PEO triblock copolymer (parts by weight/Mw) | Sucrose stearate (parts by weight) | Foaming agent (SBC) (parts by weight) | Azo-based cationic initiator (parts by weight) |
|---|---|---|---|---|
| Example 1 | 0.16/2550 | 0.016 | 0.1 | 0.1 |
| Example 2 | 0.16/2550 | 0.016 | 0.1 | 0.15 |
| Example 3 | 0.16/2550 | 0.016 | 0.1 | 0.2 |
| Example 4 | 0.28/2550 | 0.016 | 0.1 | 0.15 |
| Example 5 | 0.32/2550 | 0.016 | 0.1 | 0.15 |
| Example 6 | 0.16/2550 | 0.028 | 0.1 | 0.15 |
| Example 7 | 0.16/2550 | 0.032 | 0.1 | 0.15 |
| Example 8 | 0.16/1250 | 0.016 | 0.1 | 0.15 |
| Example 9 | 0.16/1950 | 0.016 | 0.1 | 0.15 |
| Comparative Example 1 | 0/— | 0.016 | 0.1 | 0.15 |
| Comparative Example 2 | 0.40/2550 | 0.016 | 0.1 | 0.15 |
| Comparative Example 3 | 0.16/2550 | 0.040 | 0.1 | 0.15 |
| Comparative Example 4 | 0.16/2550 | 0.016 | 0.1 | 0 |
| Comparative Example 5 | 1.6/2550 | 0.16 | 0.1 | 0.15 |
| Comparative Example 6 | 2/2550 | 0.20 | 0.1 | 0.15 |
| Comparative Example 7 | 0.16/3150 | 0.016 | 0.1 | 0.15 |
| Comparative Example 8 | 0.16/3850 | 0.016 | 0.1 | 0.15 |

Experimental Example: Evaluation of Physical Properties of Superabsorbent Polymer Physical properties of the superabsorbent polymers prepared in the examples and comparative examples were evaluated as follows.

(1) Absorption Rate (Vortex)

50 ml of a 0.9% by weight NaCl solution was added to a 100 ml beaker, and while stirring at 600 rpm using a stirrer, 2 g of each of the superabsorbent polymers prepared in the examples and comparative examples was added thereto. A time taken for the liquid vortex produced by stirring to disappear and for the liquid surface to be completely level was measured. The results were expressed as a vortex disappearance time (absorption rate; vortex).

(2) Centrifuge Retention Capacity (CRC)

Centrifuge retention capacity (CRC) by absorbency under no load was measured for the superabsorbent polymers of the examples and comparative examples in accordance with the EDANA (European Disposables and Nonwovens Association) WSP 241.3.

In detail, each polymer W0 (g) (g, about 2.0 g) of the examples and comparative examples was uniformly placed into a nonwoven-fabric-made bag, followed by sealing. Then, the bag was immersed at room temperature in a physiological saline solution which is a 0.9% by weight sodium chloride aqueous solution. After 30 minutes, the bag was drained at 250 G for 3 minutes with a centrifuge, and the weight W2 (g) of the bag was then measured. Further, the same procedure was carried out without the superabsorbent polymer, and the resultant weight W1 (g) was measured.

From these weights thus obtained, CRC (g/g) was calculated according to the following Equation:

$$CRC(g/g) = \{[W2(g) - W1(g) - W0(g)]/W0(g)\} \quad \text{[Equation 1]}$$

wherein W0 (g) is the initial weight (g) of the superabsorbent polymer, W1 (g) is the weight (g) of the apparatus, which is measured after immersing in the physiological saline solution for 30 minutes without the superabsorbent polymer and draining water off at 250 G for 3 minutes using a centrifuge, and W2 (g) is the weight (g) of the apparatus including the superabsorbent polymer, which is measured after immersing the superabsorbent polymer in the physiological saline solution at room temperature for 30 minutes and draining water off at 250 G for 3 minutes using a centrifuge.

(3) Surface Tension

All procedures were carried out in a constant temperature chamber (temperature of 23±2° C., relative humidity of 45±10%).

150 g of a physiological saline solution composed of 0.9% by weight of sodium chloride was put in a 250 mL beaker, and stirred with a magnetic bar. Each 1.0 g of the superabsorbent polymers prepared in the examples and comparative examples was added to the solution under stirring, followed by stirring for 3 minutes. After stopping stirring, the swollen superabsorbent polymer was left for 15 minutes or longer and allowed to settle to the bottom.

Thereafter, the supernatant (the solution underneath the surface) was pipetted, and transferred to another clean cup, and surface tension was measured by using a surface tension meter (Kruss K11/K100).

The same measurement was also performed for the individual base polymers which were prepared during the preparation processes of the examples and comparative examples.

The measurement results are shown in the following Table 2.

TABLE 2

| | Base polymer | | Surface-treated superabsorbent polymer | | |
|---|---|---|---|---|---|
| | CRC (g/g) | Vortex (s) | CRC (g/g) | Vortex (s) | Surface tension (mN/m) |
| Example 1 | 40.4 | 41 | 38.1 | 29 | 67.2 |
| Example 2 | 40.2 | 39 | 38.0 | 30 | 67.4 |
| Example 3 | 40.3 | 40 | 37.8 | 30 | 67.2 |
| Example 4 | 39.4 | 38 | 37.4 | 29 | 64.1 |
| Example 5 | 38.9 | 36 | 36.7 | 28 | 62 |
| Example 6 | 39.7 | 37 | 37.9 | 28 | 64.2 |
| Example 7 | 39.2 | 36 | 37.0 | 29 | 61.8 |
| Example 8 | 39.6 | 41 | 37.2 | 31 | 69.2 |
| Example 9 | 39.4 | 40 | 37.1 | 31 | 68.5 |
| Comparative Example 1 | 39.1 | 48 | 36.8 | 38 | — |
| Comparative Example 2 | 37.6 | 45 | 35.4 | 36 | — |
| Comparative Example 3 | 37.6 | 47 | 35.2 | 36 | — |
| Comparative Example 4 | 38.6 | 44 | 36.1 | 35 | — |
| Comparative Example 5 | 38.5 | 39 | 35.9 | 31 | 39.4 |
| Comparative Example 6 | 38.0 | 37 | 36.4 | 32 | 36.1 |
| Comparative Example 7 | 38.9 | 37 | 36.8 | 36 | — |
| Comparative Example 8 | 37.5 | 38 | 36.2 | 37 | — |

Referring to Table 2, the base polymers and the superabsorbent polymers prepared according to the examples of the present invention were found to have high CRC values and very fast vortex absorption rates at the same time.

In contrast, the base polymers and the superabsorbent polymers prepared according to the comparative examples were found to have low CRC values or slow vortex absorption rates. In particular, the superabsorbent polymers of Comparative Examples 5 and 6 which were prepared by using a relatively large amount of the polyalkylene oxide-based compound were found to have very small surface tension values, as compared with those of the examples of the present invention.

The invention claimed is:

1. A method of preparing a superabsorbent polymer comprising:

performing crosslinking polymerization of acrylic acid-based monomers having acidic groups which are at least partially neutralized in the presence of a polymerization initiator, a foam stabilizer, and an internal crosslinking agent to form a water-containing gel polymer;

drying, pulverizing, and size-sorting the water-containing gel polymer to form a base polymer powder; and performing surface-crosslinking of the base polymer powder by heat treatment in the presence of a surface crosslinking agent to form superabsorbent polymer particles, wherein the polymerization initiator includes a photoinitiator and a cationic azo-based initiator, and the foam stabilizer includes a sucrose ester and a polyalkylene oxide, wherein the sucrose ester is used in the amount of about 1 part by weight to about 10 parts by weight, based on 100 parts by weight of the polyalkylene oxide.

2. The method of claim 1, wherein the sucrose ester includes one or more selected from the group consisting of sucrose stearate, sucrose isobutyrate, sucrose palmitate, and sucrose laurate.

3. The method of claim 1, wherein the polyalkylene oxide includes one or more selected from the group consisting of polyethylene oxide (PEO), polypropylene oxide (PPO), a polyethylene oxide-polypropylene oxide (PEO-PPO) diblock copolymer, and a polyethylene oxide-polypropylene oxide-polyethylene oxide (PEO-PPO-PEO) triblock copolymer.

4. The method of claim 1, wherein the foam stabilizer is used in an amount of 0.001 parts by weight to 2 parts by weight, based on 100 parts by weight of the acrylic acid-based monomer.

5. The method of claim 1, wherein the cationic azo-based initiator includes one or more compounds selected from the group consisting of an azo nitrile-based initiator, an azo amide-based initiator, an azo amidine-based initiator, and an azo imidazoline-based initiator.

6. The method of claim 1, wherein the polymerization initiator is used in an amount of 0.001 parts by weight to 1 part by weight, based on 100 parts by weight of the acrylic acid-based monomer.

7. The method of claim 1, wherein the heat treatment temperature is 175° C. to 200° C.

8. The method of claim 1, wherein the crosslinking polymerization is performed by further using one or more foaming agents selected from the group consisting of sodium bicarbonate, sodium carbonate, potassium bicarbonate, potassium carbonate, calcium bicarbonate, calcium bicarbonate, magnesium bicarbonate, and magnesium carbonate.

* * * * *